United States Patent [19]

Deshmukh et al.

[11] Patent Number: 5,750,757
[45] Date of Patent: May 12, 1998

[54] PESTICIDAL ESTER PREPARATION

[75] Inventors: Abdul Rakeeb Abdul Subhan Deshmukh; Rajan Hiralal Naik; Sagun Kashinath Tandel; Srinivasachari Rajappa, all of Maharashtra, India

[73] Assignee: Council of Scientific and Industrial Research, New Delhi, India

[21] Appl. No.: 739,298

[22] Filed: Oct. 29, 1996

Related U.S. Application Data

[62] Division of Ser. No. 511,411, Aug. 4, 1995, Pat. No. 5,621,132, which is a division of Ser. No. 962,774, Oct. 19, 1992, abandoned.

[51] Int. Cl.$^6$ ................................................. C07C 333/04
[52] U.S. Cl. ...................... 558/232; 558/241; 558/242
[58] Field of Search ...................... 558/232, 241, 558/242

[56] References Cited

U.S. PATENT DOCUMENTS 3,953,427 4/1976 Matolesy et al. ................ 558/232 X

OTHER PUBLICATIONS

Kinoshita, Y. et al. "Acid Catalyzed Rearrangement of Thionocarbamates." Agr. Biol. Chem. (1966): 30(7), 710–712.

Elderfield, R.C. and F.W. Short. "Synthesis and Reactions of Certain Benzothiazoles." J. Org. Chem. (1953): 18, 1092–1103.

*Primary Examiner*—Michael G. Ambrose
*Attorney, Agent, or Firm*—Ladas & Parry

[57] ABSTRACT

A process for the preparation of an S-alkyl ester of an N-alkyl carbamothioic acid having the formula:

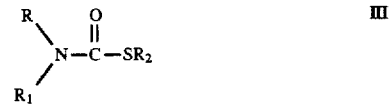

III wherein R and $R_2$ are each an alkyl group and $R_1$ is hydrogen or alkyl, which includes refluxing the corresponding alkyl ester of N-alkyl thiocarbamio acid having the formula I

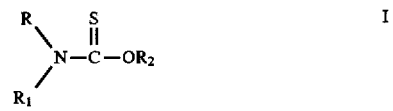

I wherein R and $R_2$ are each alkyl and $R_1$ is hydrogen or alkyl, in the presence of an acid catalyst selected from the group consisting of iodine and sulfuric acid.

5 Claims, No Drawings

PESTICIDAL ESTER PREPARATION

This is a divisional of application Ser. No. 08/511,411 filed on Aug. 4, 1995 now U.S. Pat. No. 5,421,132, which is a division of Ser. No. 07/962,774 filed on Oct. 19, 1992 now abandoned.

The present invention relates to the preparation of alkyl or aryl esters of N-alkyl or N-aryl thiocarbamic acid useful as the starting material for the preparation of S-alkyl and S-aryl esters of N-alkyl carbamothioic acid which esters, in turn, are employed as intermediates for the preparation of aryl, substituted aryl, alkyl or substituted alkyl esters of N-alkyl/aryl carbamic acid. The final carbamates find use as pesticides.

The initial thiocarbamates to which this invention relates can be represented in general by the formula:

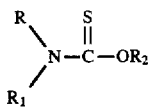

wherein R and $R_2$ are each alkyl or aryl and $R_1$ is hydrogen or alkyl.

Processes hitherto known for the preparation of these thiocarbamates have been described by A.W. Hoffman [Ber. Deutsch chem. Ges. 2,452 (1869), ibid 2,116 (1869), ibid 3,761 (1870)], W. Walter and K.D. Bode [Liebigs Ann. Chem. 698 122 (1966)] and R.P. Mull [(J Am. Chem. Soc. 77,581 (1955)]. Unfortunately, all such prior art processes suffer from the drawback that they employ hazardous and corrosive chemicals such as isothiocyanates or chlorothioformates.

Likewise, prior art processes for the preparation of the final aryl, substituted aryl, alkyl or substituted alkyl carbamates are also known to employ hazardous, toxic substances such as phosgene and methyl isocyanate for their preparation. Prior art processes which employ phosgene for such carbamate production are described in U.S. Patents Nos. 2,903,478 and 3,009,855. Those which employ methyl isocyanate are best exemplified by U.S. Patent Nos. 3,474,170, 3,474,171, 3,356,690 and 3,111,539.

The drawbacks to such prior art processes for the production of both the thiocarbamates and the carbamates are aggravated by the fact that the toxic substances such as alkylisocyanate, chlorothioformate, and methylisocyanate are produced in the initial step thus entailing the provision of stringent precautions against accident and injury. Thus, apart from the risk factor involved, the additional precautionary provisions that needs must be made render the known processes exceedingly uneconomical. Added to this, are the further problems of high temperature provision for pyrolysis and the recycling of reactants.

With a view to avoiding shortcomings of the prior art, copending Indian Patent Application No. 284/Del/89 proposes a process for the preparation of methyl N-methylcarbamate of the formula:

$$CH_3NH—COOR \qquad V$$

wherein R is $CH_3$ by the oxidative carbonylation of methylamine employing carbon monoxide in the presence of methanol and converting the resulting product into any aryl or substituted aryl N-methylcarbamate by irreversible transesterification employing halogen-containing phosphorus compound. Unfortunately, even this process employs carbon monoxide which although not as toxic and hazardous as phosgene or methylisocyanate, is still not a safe chemical.

It is in this context that the present invention aims to do totally away with the employment of hazardous reactants in the production of both the initial thiocarbamates and the final carbamates. To the applicants' knowledge, it has never been known first of all to prepare thiocarbamates from an innocuous S-aryl or S-alkyl dithiocarbamate. Moreover, the produced thiocarbamates can on rearrangement provide the corresponding S-alkyl or S-aryl carbamothioates which can thereafter be employed as intermediates for the preparation of the final pesticidal carbamates.

With regard to such intermediates, it is known that the S-alkyl ester of N-alkyl carbamothioic acid can be produced by employing acid catalysts such as $BF_3$/etherate and p-toluene sulphonic acid [Agri. Biol. Chem. 36, 1975–1981, 1972 and Agri. Biol. Chem. 30, 710–712, 1966]. The drawbacks to these processes is that it is essential that they be carried out with either equimolar or considerable excess amounts of such catalysts despite very low yields of the resultant rearranged products.

In a first embodiment, therefore, the present invention provides a process for the preparation of alkyl esters of N-alkyl or N-aryl thiocarbamic acid having the formula:

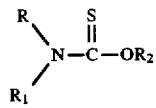

wherein R and $R_2$ are each alkyl or aryl and $R_1$ is hydrogen or alkyl which comprises reacting the S-alkyl or S-aryl ester of N-alkyl or aryl dithiocarbamic acid having the formula:

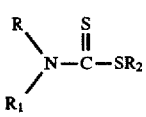

wherein R, $R_1$ and $R_2$ have the meanings stated above with an appropriate alkali metal alkoxide in the presence of one or more alcoholic solvents.

A particularly preferred thiocarbamate is the alkyl ester of N-methylthiocarbamic acid having the formula I wherein R is methyl or aryl, $R_1$ is hydrogen or methyl and $R_2$ is an alkyl or aryl group. This preferred compound results from the reaction of the compound of formula II wherein R is methyl or aryl, $R_1$ is hydrogen or methyl and $R_2$ is alkyl with the alkali metal alkoxide.

The starting compound, i.e. the S-alkyl ester of N-alkyldithiocarbamic acid of formula II wherein $R_2$ is alkyl can conveniently be prepared by the general procedure described by A.D. Ainley et al. [J.C.S., 1947, 147]. More specifically, the S-methyl ester of N-methyldithiocarbamic acid of formula II wherein R and $R_2$ are each methyl and $R_1$ is hydrogen has in the past been prepared by reacting carbon disulphide with methylamine in the presence of an alkali hydroxide followed by methylation of the resulting product with dimethylsulphate.

When such S-methyl ester of N-methyl dithiocarbamic acid is employed, the preferred alkali metal alkoxide is sodium methoxide and the preferred solvent is methanol.

Preferably, the reaction of the dithiocarbamate of formula II with the alkali metal alkoxide is effected at a temperature in the range of from 65° C. to 85° C. over a period of from 15 to 25 hours.

According to a further embodiment, the present invention provides a process for the preparation of S-alkyl and S-aryl esters of N-alkyl carbamothioic acid having the formula:

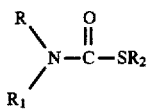

III wherein R and $R_2$ are each an alkyl or aryl group and $R_1$ is hydrogen or alkyl which comprises refluxing the corresponding alkyl or aryl esters of N-alkyl thiocarbamic acid having the formula I wherein R and $R_2$ are each alkyl and $R_1$ is hydrogen in the presence of an acid catalyst.

Examples of the preferred acid catalyst include iodine and sulphuric acid.

For convenience, the refluxing can be effected in a solvent or mixture of solvents selected 20 from benzene, chloroform, dichloroethane or the like at a temperature in the range of from 65° C. to 120° C. over a period of from 8 to 15 hours.

In its final embodiment, the present invention provides a process for the preparation of aryl, substituted aryl, alkyl or substituted alkyl esters of N-alkyl/aryl carbamic acid having the formula:

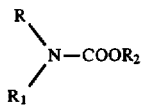

IV wherein R is alkyl or aryl and $R_1$ is hydrogen or alkyl which comprises reacting the corresponding S-aryl, S-substituted aryl, S-alkyl or S-substituted alkyl ester of N-alkyl carbamothioic acid having the formula III wherein R and $R_2$ are each an alkyl or aryl group and $R_1$ is hydrogen or alkyl with an appropriately substituted phenol in an organic solvent in the presence of a catalyst for the reaction.

According to a preferred reaction, the appropriately substituted phenol can be reacted with the corresponding S-aryl, S-substituted aryl, S-alkyl or S-substituted alkyl esters of N-aryl, N-substituted aryl, N-alkyl or N-substituted alkyl dithiocarbamic acid of the formula II wherein R is aryl, substituted aryl, alkyl or substituted alkyl, $R_1$ is hydrogen or alkyl and $R_2$ is alkyl.

According to a preferred embodiment, the substituted phenol is substituted with from one to three substituting groups equal or different to each other, said substituting groups being selected from alkyl, oxyalkyl, thioalkyl, aminoalkyl, alkylene- oxyalkyl, alkylene-thioalkyl and alkylene-aminoalkyl groups wherein the alkyl group is a straight or branched group containing from 1 to 5 carbon atoms and the alkylene group contains from 1 to 2 carbons atoms, 2-sec. butyl and isopropyl.

More preferably, the substituted phenol employed is selected from 2,3-dihydro-2,2-dimethyl-benzofuran-7-ol; 2,2-dimethyl-1,3-benzodioxol-4-ol; 2-(1,3-dioxolan-2-yl)-phenol; 1-naphthol, 2-naphthol or 2-isopropoxyphenol.

The catalyst employed for preparation of the carbamates is selected from sodium triethylamine, iodine, sulphuric acid or mixtures thereof.

The organic solvent for the reaction can be selected from benzene, acetonitrile, chloroform or mixtures thereof.

As stated, the carbamates resulting from the final embodiment of the invention find use as pesticides. A particularly important pesticide is the ester of N-methylcarbamic acid of the general formula:

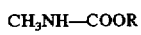

V wherein R represents an aryl, substituted aryl, alkyl or substituted alkyl group.

Examples of other pesticidal compounds falling within the scope of general formula IV are as follows:

2-sec-butylphenyl N-methylcarbamate of the formula:

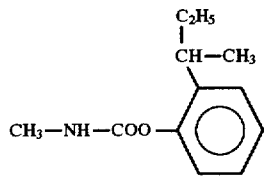

VI 1-naphthol N-methylcarbamate of the formula:

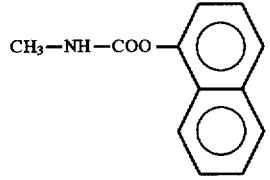

VII 2,3-dihydro-2, 2-dimethyl-7-benzofuranyl N-methylcarbamate of the formula:

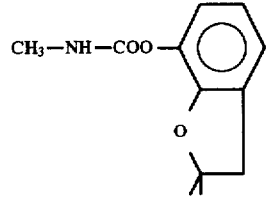

VIII 2-isopropoxyphenyl N-methylcarbamate of the formula:

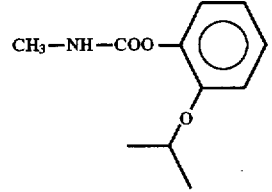

IX 2-isopropylphenyl N-methylcarbamate of the formula:

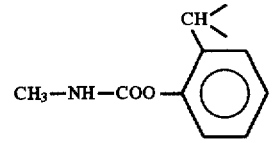

X

The invention will now be described in greater detail in the following Examples:

EXAMPLE 1

Preparation of methyl N-methylthiocarbamic acid of the formula I where R=$R_2$=$CH_3$, $_1$=H To a solution of methoxide (2g. sodium in 200ml methanol) there was added S-methyl ester of N-methyldithiocarbamic acid of the formula II (60 g) and the mixture was refluxed for 20 hr. After the reaction was over, most of the methanol was distilled off under vacuum and the liquid residue was taken in dichloromethane (500 ml) and washed with water, brine, and dried over sodium sulphate. Removal of solvent afforded the liquid residue which was further purified by distillation to afford methyl N-methylthiocarbamate of the formula (I) where R=$R_2$= methyl, $R_1$=H; b.p. 100/2 mm, IR:3140 (N-H), 1530 (-CS-); PMR: (90 MHz, CdCl$_3$): 2.84, 3.06 (3H each, d each, J=7Hz each, rotational isomers of $NH-CH_3$) and 3.95, 4.06 (3H, s each, rotational isomers of $O-CH_3$).

EXAMPLE 2

Ethyl-N-methylthiocarbamic acid of the formula I where R=methyl, $R_1$=H, $R_2$=ethyl To a solution of methoxide (2.5 g of sodium in 200 ml methanol) there was added S-methyl ester of N-methyldithiocarbamic acid of the formula II (60 g) and the mixture was refluxed for 20 hr. After the reaction was over, the reaction mixture was worked up as described earlier to give liquid residue which was further purified by distillation to afford ethyl-N-methylthiocarbamic acid of the formula I where R=methyl, $R_1$=H and $R_2$=ethyl.

EXAMPLE 3

Preparation of S-methyl ester of N-methylcarbamothioic acid of the formula III where R=$R_2$ methyl and $R_1$=H To a solution of methyl N-methylthiocarbamate (10.5 g, 0.1 mole) in benzene (80 ml) there were added iodine crystals (0.5 g) and the mixture was refluxed for 20 hr. After the reaction was over, the reaction mixture was washed with sodium thiosulphate solution followed by brine and dried. Removal of solvent afforded the liquid residue which was further purified by distillation to give S-methyl ester of N-methylcarbamothioic acid of the formula III where R=$R_2$=methyl and $R_1$=H; IR: 3300 (N-H), 1650 (-CO-) PMR (60 MHz, $CdCl_3$): 2.31 (3H, s, S-$CH_3$ protons), 2.84 (3H, d, J=7 Hz, NH-$CH_3$) and 4.85 (1H, hump, N-H).

EXAMPLE 4

Preparation of S-methylester of N-methylcarbamothioic acid of the formula III where R=$CH_3$,$R_1$=H and $R_2$=$CH_3$ To a solution of methyl N-methylthiocarbamate (1.05 g, 0.01 mole) in chloroform (6 ml) there was added concentrated $H_2SO_4$ (0.2 ml) and the mixture was refluxed for 10 hrs. The reaction mixture was cooled and washed with water and brine. Chloroform was distilled off and the liquid residue was distilled to give pure S-methyl ester of N-methylcarbamothioic acid of the formula III, where R=$CH_3$, $R_1$=H and $R_2$=$CH_3$.

EXAMPLE 5

Preparation of S-methylester of N-ethylcarbamothioic acid of the formula III where R=ethyl, $R_1$=H and $R_2$=methyl To a solution of methyl N-ethylthiocarbamate (11.9 g, 0.1 mole) in chloroform (80 ml) there were added concentrated sulphuric acid (0.5 ml) and the mixture was refluxed for 20 hrs. After the reaction was over, the reaction mixture was washed with water and brine and dried over anhydrous sodium and further purified by distillation to give the title compound.

EXAMPLE 6

Preparation of methyl N-methyl carbamate of the formula V where R=$CH_3$

To a solution of methyl N-methylthiocarbamate (10.5 g, 0.1 mole) in benzene (80 ml) there were added iodine crystals (0.5 g) and the reaction mixture was refluxed for 19 hrs. After the reaction was over, benzene was distilled off under vacuum and the residue was added to freshly prepared sodium ethoxide (1 g Na in 100 ml $CH_3OH$) and refluxed for 15 hr. Methanol was then evaporated and the residue was taken in dichloromethane (60 ml) and washed with water and brine, dried over anhydrous sodium sulphate. After removal of solvent, the liquid residue obtained was further purified by distillation to give methyl N-methylcarbamate of the formula V where R=$CH_3$, b.p. 85° C./4 mm, IR: 3300 (N-H), 1685 (-CO-), PMR ($CdCl_3$, 90 MHz): 2.78 (3H, s, NH-$CH_3$), 3.68 (3H, s, $OCH_3$) and 4.85 (1H, hump, N-H proton).

EXAMPLE 7

Preparation of 2-Sec. butylphenyl N-methylcarbamate of the formula VI

To a solution of 2-Sec. butylphenol (1.5 g, 0.01 mole) 0.2 ml of $Et_3N$ was added under stirring. S-methyl ester of N-methylcarbamothioic acid (1.05 g, 0.01 mole) in acetonitrile (10 ml) was added dropwise over a period of 4 hrs, keeping reflux temperature. After 30 hr, acetonitrile was evaporated under vacuum. The residue was taken in dichloromethane (25 ml), washed with water and a 5% cold NaOH solution, followed by water and brine and dried over sodium sulphate. After removal of the solvent, the liquid residue obtained was further purified by distillation to give 2-Sec. butylphenyl N-methylcarbamate of the formula VI; IR: 3329 (N-H), 1730 (-COO), 1535, 1490 and 750 (aromatic); PMR ($CdCl_3$, 90 MHz): 0.81 (3H, 1, primary methyl of side chain), 1.18 (3H, d, J=7Hz, secondary/methyl of side chain), 1.58 (2H, m, methylene protons of side chain), 2.88 (4H, doublet overlapping a multiplet, NH- $CH_3$ and benzylic proton), 4.97 (1H, br s, N H) and 6.95 to 7.25 (4H, m, aromatic).

EXAMPLE 8

1 Naphthyl N-methylcarbamate of the formula VII

To a solution of 1-naphthol (1.44 g, 0.01 mole) and S-methyl ester of N-methylcarbamothioic acid (1.575 g, 0.015 mole) in benzene (6 ml) there was added sodium (0.15 g) and the mixture was refluxed for 20 hrs. The reaction mixture was cooled and washed with water and a cold 5% NaOH solution followed by water and brine and then dried. The removal of solvent afforded the solid which was further purified by crystallization to furnish 1-naphthyl N-methylcarbamate of the formula VII, m.p. 140–141° C., IR: 3305 (N-H), 1715 (-COO-), 1600, 1540, 770 (aromatic): PMR ($CdCl_3$, 90 MHz), 2.86 (3H, d, J=1Hz, NH-$CH_3$, 5.14 (1H, br s, N-H) and 7.17 to 8 (7H, m, aromatic).

EXAMPLE 9

2-Isopropoxyphenyl N-methylcarbamate of the formula IX

To a solution of 2-isopropoxyphenyl (1.52 g, 0.01 mole) and S-methyl ester of N-methylthio-carbamothioic acid (1.05 g, 0.01 mole) in benzene (6 ml) there was added triethylamine (0.2 ml) and the mixture was refluxed for 15 hrs. The reaction mixture was worked up as described earlier to give 2-isopropoxy-phenyl N-methylcarbamate of the formula IX as a solid, crystallized from petroleum ether, m.p. 89°–90°.

EXAMPLE 10

Preparation of 2-Isopropylphenyl N-methylcarbamate of the formula X

To a solution of 2-isopropylphenyl (1.38 g, 0.01 mole) and S-methylester of N-methylcarbamothioic acid (1.05 g, 0.01 mole) in dichloroethane there was added triethylamine (0.5 g) and the mixture was refluxed for 12 hr. The reaction mixture was worked up as described earlier to give 2-isopropylphenyl N-methylcarbamate of the formula X as a solid, crystallized from pet. ether, m.p. 88°–93° C.

Having now described the invention in detail, what the applicants claim is set out hereafter.

We claim:

1. A process for the preparation of an S-alkyl ester of an N-alkyl carbamothioic acid having the formula:

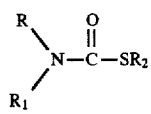   III wherein R and $R_2$ are each an alkyl group and $R_1$ is hydrogen or alkyl, which comprises refluxing the corresponding alkyl ester of N-alkyl thiocarbamic acid having the formula I

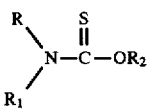   I wherein R and $R_2$ are each alkyl and $R_1$ is hydrogen or alkyl, in the presence of an acid catalyst selected from the group consisting of iodine and sulfuric acid.

2. A process as claimed in claim 1, wherein the refluxing is effected at a temperature in the range of solvents selected from benzene, chloroform, and dichloroethane.

3. A process as claimed in claim 1, wherein the refluxing is effected at a temperature in the range of 65° C. to 120° C. for a period of from 8 to 15 hours.

4. A process as claimed in claim 3 wherein the acid catalyst is iodine.

5. A process a claimed in claim 3 wherein the acid catalyst is sulfuric acid.

* * * * *